(12) United States Patent
Hiwatashi et al.

(10) Patent No.: US 8,606,532 B2
(45) Date of Patent: Dec. 10, 2013

(54) FRACTURE DETERMINATION METHOD, FRACTURE DETERMINATION APPARATUS, PROGRAM, AND COMPUTER READABLE RECORDING MEDIUM

(75) Inventors: Shunji Hiwatashi, Tokyo (JP); Shigeru Yonemura, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 0 days.

(21) Appl. No.: 13/634,341

(22) PCT Filed: Apr. 6, 2011

(86) PCT No.: PCT/JP2011/058739
§ 371 (c)(1),
(2), (4) Date: Sep. 12, 2012

(87) PCT Pub. No.: WO2011/126058
PCT Pub. Date: Oct. 13, 2011

(65) Prior Publication Data
US 2013/0006543 A1     Jan. 3, 2013

(30) Foreign Application Priority Data

Apr. 7, 2010 (JP) .................................. 2010-088269

(51) Int. Cl.
*G06F 19/00* (2011.01)
*G01L 1/00* (2006.01)
(52) U.S. Cl.
USPC ............................................................ 702/42
(58) Field of Classification Search
USPC ....................................................... 702/42
See application file for complete search history.

(56) References Cited

U.S. PATENT DOCUMENTS

| | | | |
|---|---|---|---|
| 4,299,120 A | 11/1981 | Barker | |
| 4,733,567 A | 3/1988 | Serata | |
| 8,494,827 B2 * | 7/2013 | Mutlu et al. | 703/10 |
| 2009/0177417 A1 | 7/2009 | Yonemura et al. | |
| 2011/0077918 A1 * | 3/2011 | Mutlu et al. | 703/2 |
| 2011/0191074 A1 * | 8/2011 | Holdbrook | 703/2 |

FOREIGN PATENT DOCUMENTS

| | | |
|---|---|---|
| CN | 1995962 | 7/2007 |
| EP | 1 785 716 | 5/2007 |
| EP | 1 985 989 | 10/2008 |
| JP | 2000-301262 | 10/2000 |

(Continued)

OTHER PUBLICATIONS

International Search Report dated Jun. 28, 2011 issued in corresponding PCT Application No. PCT/JP2011/058739.

(Continued)

*Primary Examiner* — Bryan Bui
(74) *Attorney, Agent, or Firm* — Kenyon & Kenyon LLP

(57) ABSTRACT

A fracture determination method for determining a fracture of a metal structure includes, when a fracture determination target portion has returned from a plastic state to an elastic state, given that a stress when the portion returned to the elastic state is $(x, y)=(\sigma 2, \sigma 1)$ (maximum principal stress: $\sigma 1$, minimum principal stress: $\sigma 2$) on a $(x, y)$ coordinate plane, performing fracture determination of the fracture determination target portion using a re-yield stress R determined by the intersection between a straight line satisfying a relation $y=(\sigma 1/\sigma 2)x$ and an yield curve obtained from the plastic state of the fracture determination target portion. Fracture determination can be performed with high accuracy even when the fracture determination target portion has returned from a plastic state to an elastic state.

7 Claims, 9 Drawing Sheets

(56) References Cited

FOREIGN PATENT DOCUMENTS

| JP | 2000-312933 | 11/2000 |
|----|-------------|---------|
| JP | 2004-042098 | 2/2004 |
| JP | 2006-155254 | 6/2006 |
| JP | 2007-152407 | 6/2007 |
| JP | 2007-232714 | 9/2007 |
| JP | 2007-232715 | 9/2007 |
| JP | 2007-285832 | 11/2007 |

OTHER PUBLICATIONS

Shigeru Yonemura et al., "Forming Limit Prediction and Work-hardening Behavior under Strain-path Changes", Journal of the Iron & Steel Institute of Japan, Apr. 1, 2007, vol. 93, No. 4, pp. 317 to 323.

Shigeru Yonemura et al., "Improvement of Impact Energy Absorption by Using High Strength Steel, Part VIII-Forming Limit Prediction under Strain-path Changes for Automotive High Strength Steels-", Preprints of Meeting on Automotive Engineers, May 23, 2007, No. 21-07, pp. 1 to 4.

International Preliminary Report on Patentability dated Nov. 15, 2012 issued in corresponding PCT Application No. PCT/JP2011/058739.

Extended European Search Report dated Oct. 8, 2013 issued in corresponding EP Application No. 11 76 5958.

A.G. Mamalis et al., "Prediction of the limit strains of steel sheet thermally and mechanically worked in relation to surface integrity changes: A theoretical model", Journal of Materials Processing Technology, vol. 25, No. 1, Feb. 1, 1991, pp. 15-33.

H. Vegter et al., "Influence Of The Plastic Material Behaviour On The Prediction Of Forming Limits", AIP Conference Proceedings, vol. 908, Jan. 1, 2007, pp. 87-92.

Katusimi et al., "Estimation of a Macro Crack Trajectory in Orthogonal Cutting of Ceramics by the Finite Element Method", Journal of the Society of Materials Science, Japan, vol. 32, No. 363, Jan. 1, 1983, pp. 1327-1333.

Chinese Office Action dated Jul. 19, 2013 issued in corresponding Chinese Application No. 201180016980.9.

\* cited by examiner

FRACTURE DETERMINATION METHOD, FRACTURE DETERMINATION APPARATUS, PROGRAM, AND COMPUTER READABLE RECORDING MEDIUM

This application is a national stage application of International Application No. PCT/JP2011/058739, filed 6 Apr. 2011, which claims priority to Japanese Application No. 2010-088269, filed 7 Apr. 2010, which is incorporated by reference in its entirety.

TECHNICAL FIELD

The present invention relates to a fracture determination method, a fracture determination apparatus, a program, and a computer readable recording medium for determining a fracture of a metal sheet, a part formed of a metal sheet, and a structure formed of a metal sheet, and the like in a collision simulation of an automobile, a stamping simulation of a part, or the like.

BACKGROUND ART

In recent years, in automotive industry, developing a vehicle body structure capable of reducing injury to passengers in collision is an urgent issue. A vehicle body structure excelling in such collision safety can be achieved by absorbing impact energy in the event of collision by structural members other than the passenger compartment, so as to minimize deformation of the passenger compartment and secure a survival space.

That is, it is important to enable the structural members to absorb impact energy. To improve absorption of impact energy, it is crucial to stabilize a buckling mode and to prohibit bending or fracture in the middle, and it is necessary to accurately evaluate what degree of fracture risk has been reached at the present moment.

However, in a collision or stamping of an automobile, each member goes through a complicated deformation path, and thus the fracture risk varies depending on its deformation history. Therefore, it has been difficult to accurately evaluate the fracture risk per portion of each member.

There have conventionally been many proposals of methods and apparatuses and the like for predicting a fracture. For example, Japanese Laid-open Patent Publication No. 2007-152407 (Patent Document 1 below) discloses an arithmetic processing apparatus which predicts a fracture in stamping by using a stamping simulation means, an equivalent plastic strain calculation means, a formation crack determination value calculation means, and a formation crack determination means. The formation crack determination means of the arithmetic processing apparatus is capable of predicting a formation crack more accurately when predicting a formation crack with reference to a formation limit diagram by predicting a formation crack by whether or not a determination target equivalent plastic strain exceeds a formation crack determination value in the proceeding direction of the strain. However, the method of Patent Document 1 is to evaluate a fracture margin by the distance to a non-proportional formation limit value in a strain space, and the method needs to recalculate the non-proportional formation limit value every time the proceeding direction of the strain changes, and hence is complicated.

Further, Japanese Laid-open Patent Publication No. 2007-232714 (Patent Document 2 below) discloses that, with a line obtained by converting a hole expanding ratio into a stress being taken as a fracture limit stress line, the fracture risk of a material is quantitatively evaluated by comparing the relation between data obtained from a numerical analysis using a finite element method and the fracture limit stress line. In the method of Patent Document 2, it is possible to easily and efficiently obtain a fracture limit line when determining the fracture limit of a thin sheet in a process including one or more deformation path variations, and determine a fracture limit with high prediction accuracy.

Further, Japanese Laid-open Patent Publication No. 2007-232715 (Patent Document 3 below) discloses that, with a line obtained by converting a hole expanding ratio into a stress being taken as a fracture limit stress line, the fracture risk of a material is quantitatively evaluated by comparing the relation between data obtained from a numerical analysis using a finite element method and the fracture limit stress line. In the method of Patent Document 3, it is possible to easily and efficiently obtain a fracture limit line when determining the fracture limit of a stretch flange part in a thin sheet in a process including one or more deformation path variations, and determine a fracture with high accuracy, thereby allowing evaluation of the risk of fracture during stamping or in the event of collision.

Moreover, Japanese Laid-open Patent Publication No. 2007-285832 (Patent Document 4 below) discloses a fracture limit obtaining system in which a user terminal provides material data as the target of fracture determination to a server and obtain data of a fracture limit line from the server. It discloses that the user terminal quantitatively evaluates the fracture risk of a material using the obtained fracture limit line.

CITATION LIST

Patent Literature

Patent Literature 1: Japanese Laid-open Patent Publication No. 2007-152407
Patent Literature 2: Japanese Laid-open Patent Publication No. 2007-232714
Patent Literature 3: Japanese Laid-open Patent Publication No. 2007-232715
Patent Literature 4: Japanese Laid-open Patent Publication No. 2007-285832

SUMMARY OF INVENTION

Technical Problem

However, although the above-described Patent Documents 2 to 4 can correspond to non-proportional deformation by evaluation with stress, they do not specifically present quantitative indexes representing the degree of risk of fracture. Further, in a simple fracture determination method there is a problem that the fracture risk varies if the metal structure has returned from a plastic state to an elastic state.

The present invention is made in view of the problems of conventional arts as described above, and it is an object thereof to provide a fracture determination method, a fracture determination apparatus, a program, and a computer readable recording medium which are capable of performing fracture determination with high accuracy even when the metal structure has returned from a plastic state to an elastic state.

Solution to Problem

The present invention is a fracture determination method for determining a fracture of a metal structure, the method including: a deformation analyzing step of performing deformation analysis from start of deformation to end of deformation of the metal structure; and a fracture determination step of extracting a fracture determination target portion from a deformation state of the metal structure obtained in the deformation analyzing step, and when the extracted fracture determination target portion has returned from a plastic state to an elastic state, given that a stress when the portion returned to the elastic state is (x, y)=(σ2, σ1) (maximum principal stress: σ1, minimum principal stress: σ2) on a (x, y) coordinate plane, performing fracture determination of the fracture determination target portion using a re-yield stress determined by an intersection between a straight line satisfying a relation y=(σ1/σ2)x and an yield curve obtained from the plastic state of the fracture determination target portion.

Further, the present invention is a fracture determination apparatus determining a fracture of a metal structure, the apparatus including: a deformation analyzing unit performing deformation analysis from start of deformation to end of deformation of the metal structure; and a fracture determination unit extracting a fracture determination target portion from a deformation state of the metal structure obtained in the deformation analyzing unit, and when the extracted fracture determination target portion has returned from a plastic state to an elastic state, given that a stress when the portion returned to the elastic state is (x, y)=(σ2, σ1) (maximum principal stress: σ1, minimum principal stress: σ2) on a (x, y) coordinate plane, performing fracture determination of the fracture determination target portion using a re-yield stress determined by an intersection between a straight line satisfying a relation y=(σ1/σ2)x and an yield curve obtained from the plastic state of the fracture determination target portion.

Further, the present invention is a program for determining a fracture of a metal structure, the program causing a computer to execute: a deformation analyzing step of performing deformation analysis from start of deformation to end of deformation of the metal structure; and a fracture determination step of extracting a fracture determination target portion from a deformation state of the metal structure obtained in the deformation analyzing step, and when the extracted fracture determination target portion has returned from a plastic state to an elastic state, given that a stress when the portion returned to the elastic state is (x, y)=(σ2, σ1) (maximum principal stress: σ1, minimum principal stress: σ2) on a (x, y) coordinate plane, performing fracture determination of the fracture determination target portion using a re-yield stress determined by an intersection between a straight line satisfying a relation y=(σ1/σ2)x and an yield curve obtained from the plastic state of the fracture determination target portion.

Further, the present invention is a computer readable recording medium recording a program for determining a fracture of a metal structure, the program causing a computer to execute: a deformation analyzing step of performing deformation analysis from start of deformation to end of deformation of the metal structure; and a fracture determination step of extracting a fracture determination target portion from a deformation state of the metal structure obtained in the deformation analyzing step, and when the extracted fracture determination target portion has returned from a plastic state to an elastic state, given that a stress when the portion returned to the elastic state is (x, y)=(σ2, σ1) (maximum principal stress: σ1, minimum principal stress: σ2) on a (x, y) coordinate plane, performing fracture determination of the fracture determination target portion using a re-yield stress determined by an intersection between a straight line satisfying a relation y=(σ1/σ2)x and an yield curve obtained from the plastic state of the fracture determination target portion.

Advantageous Effects of Invention

According to the present invention, fracture determination can be performed with high accuracy even when a fracture determination target portion of a metal structure has returned from a plastic state to an elastic state.

DESCRIPTION OF EMBODIMENTS

Hereinafter, preferred embodiments of the present invention will be described with reference to the attached drawings.

Figure 1:
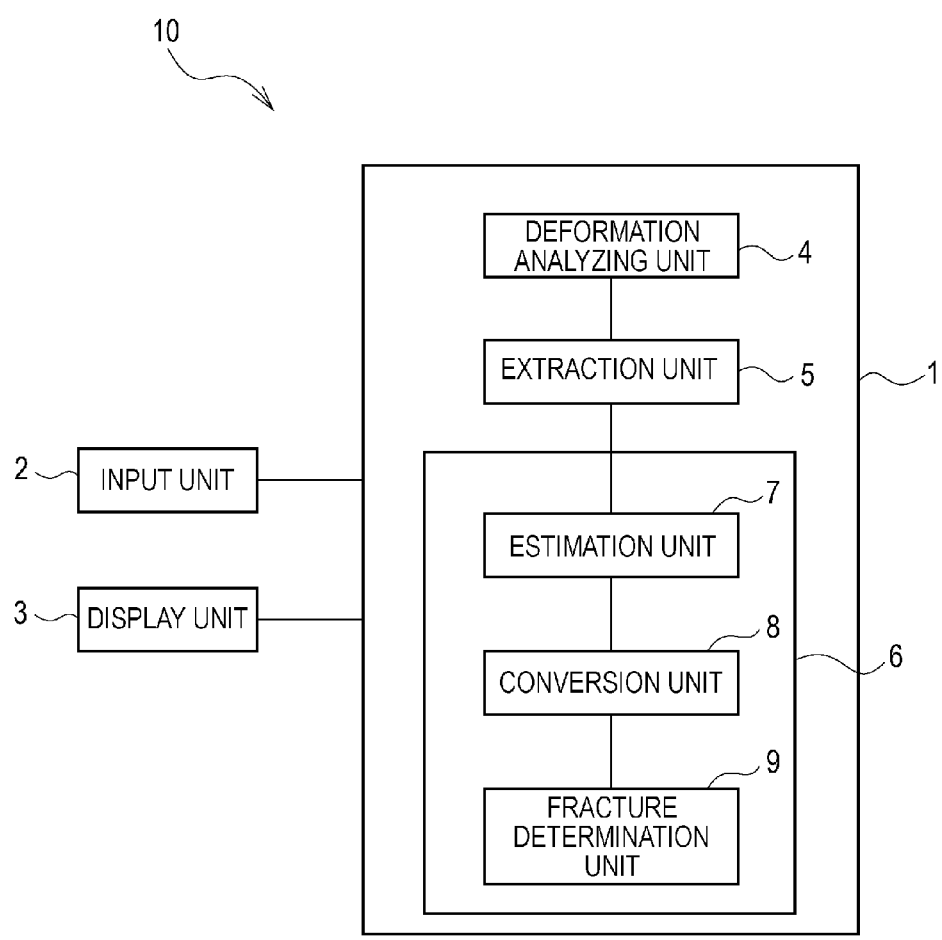
FIG. 1 is a diagram illustrating a functional structure of a fracture determination apparatus.

FIG. 1 is a diagram illustrating a functional structure of a fracture determination apparatus 10 according to this embodiment. The fracture determination apparatus 10 includes a fracture determination main unit 1, an input unit 2, and a display unit 3. The fracture determination main unit 1 includes a deformation analyzing unit 4, an extraction unit 5, and a fracture analyzing unit 6. The fracture analyzing unit 6 includes an estimation unit 7, a conversion unit 8, and a fracture determination unit 9.

The fracture determination apparatus 10 of this embodiment simulates a sequence of deformation from start of deformation to end of deformation of a metal sheet, a part made of a metal sheet, and a structure made of a metal sheet (hereinafter referred to as a metal structure). The fracture determination apparatus 10 extracts a fracture determination target portion as the target of fracture determination from the deformation state of the metal structure at arbitrary timing corresponding to a fracture determination mode, and performs fracture determination with respect to this fracture determination target portion.

In a first fracture determination mode, after a deformation analysis is performed from the start of deformation to the end of deformation of the metal structure, the fracture determination target portion is extracted from the deformation state in one or more arbitrary or predetermined steps, and performs fracture determination with respect to the extracted fracture determination target portion.

In a second fracture determination mode, a deformation analysis is performed from the start of deformation of the metal structure and subsequently the fracture determination target portion is extracted from the deformation state thereof, fracture determination with respect to the extracted fracture determination target portion is performed, and the deformation analysis and the fracture determination are repeated until the end of deformation.

First, a fracture determination method in the first fracture determination mode will be described with reference to the flowchart illustrated in FIG. 2. Here, in the fracture determination apparatus 10, the material and mechanical characteristic values, and so on of the metal structure are stored in advance, and it is ready for simulation.

Assuming that a predetermined stress is applied to a predetermined position of the metal structure, the deformation analyzing unit 4 starts deformation analysis of the metal structure in response to an instruction from the input unit 2 (S21). The deformation analyzing unit 4 performs the deformation analysis in steps at every predetermined time or at every time determined according to the degree of deformation. Further, the deformation analyzing unit 4 uses an approach such as a finite element method for each step to sequentially analyze the deformation state of stress, strain, or the like occurring in the metal structure, and performs deformation analysis in the next step based on this deformation state (S22). For example, one portion of the metal structure changes from an elastic state to a plastic state or returns from a plastic state to an elastic state, as will be described later. The deformation analyzing unit 4 performs the deformation analysis until the end of deformation of the metal structure (S23). The deformation analyzing unit 4 stores the deformation state of the metal structure obtained by the deformation analysis in every step. Note that in a practical analysis of a metal structure, the number of steps can be, for example, several ten thousands of steps to several millions of steps.

Next, the extraction unit 5 extracts the deformation state of one or more arbitrary or predetermined steps from the stored deformation states, and extracts an arbitrary or predetermined fracture determination target portion from the extracted deformation state (S24). The deformation state to be extracted is the deformation state of a step which is arbitrarily inputted via the input unit 2 by the user, or the deformation state of a predetermined step. Further, the fracture determination target portion to be extracted is a fracture determination target portion which is arbitrarily inputted via the input unit 2 by the user, or a predetermined fracture determination target portion. The fracture determination target portion to be extracted can be all portions of the metal structure. Further, for the deformation state of the step to be extracted, although it is desired to extract the deformation states of all steps for finding out a fracture state, it is preferred to extract the deformation state in every 10 steps to 1000 steps for increasing calculation efficiency.

The fracture analyzing unit 6 performs fracture determination of each extracted fracture determination target portion (steps S25, S26). Note that details of the fracture determination by the fracture analyzing unit 6 will be described later. The fracture analyzing unit 6 stores the fracture determination of the fracture determination target portion and finishes the fracture determination.

In the first fracture determination mode, the deformation state of one or more steps is extracted after the deformation analysis from the start of deformation to the end of determination of the metal structure, an arbitrary or predetermined fracture determination target portion is extracted from the extracted deformation state, and fracture determination is performed for the extracted fracture determination target portion. Therefore, fracture determination in an arbitrary step is possible when the fracture determination target portion of the metal structure is in either of an elastic state and a plastic state. Further, since fracture determination of an arbitrary fracture determination target portion can be performed, the user can comprehend a local strength of the metal structure.

Next, a fracture determination method in the second fracture determination mode will be described with reference to the flowchart illustrated in FIG. 3. Here, in the fracture determination apparatus 10, the material and mechanical characteristic values, and so on of the metal structure are stored in advance, and it is ready for simulation.

Assuming that a predetermined stress is applied to a predetermined position of the metal structure, the deformation analyzing unit 4 starts deformation analysis of the metal structure in response to an instruction from the input unit 2 (S31). The deformation analyzing unit 4 performs the deformation analysis in steps at every predetermined time or at every time determined according to the degree of deformation. Further, the deformation analyzing unit 4 uses an approach such as a finite element method for each step to sequentially analyze the deformation state of stress, strain, or the like occurring in the metal structure, and performs deformation analysis in the next step based on this deformation state (S32, S33). For example, one portion of the metal structure changes from an elastic state to a plastic state or returns from a plastic state to an elastic state, as will be described later. The deformation analyzing unit 4 stores the deformation state of the metal structure obtained by the deformation analysis in every step.

Then, the extraction unit 5 extracts an arbitrary or predetermined fracture determination target portion from the deformation state of the metal structure after a predetermined step interval (S34). Note that although the step interval may be one step interval or arbitrary step intervals, it is preferred to be every 10 steps to 1000 steps for increasing calculation efficiency. Further, the fracture determination target portion to be extracted is a fracture determination target portion which is arbitrarily inputted via the input unit 2 by the user, or a predetermined fracture determination target portion. The fracture determination target portion to be extracted can be all portions of the metal structure. Note that the flowchart illustrated in FIG. 3 describes a method to perform the fracture analysis after a two-step interval.

Next, the fracture analyzing unit 6 performs fracture determination of the extracted fracture determination target portion (S35). Note that details of the fracture determination by the fracture analyzing unit 6 will be described later. The fracture analyzing unit 6 stores the fracture determination of the fracture determination target portion.

Thereafter, similarly, subsequent to the deformation analysis after the predetermined step interval (S36, S37), the extraction unit 5 extracts an arbitrary or predetermined fracture determination target portion from the deformation state of the metal structure (S38). The fracture analyzing unit 6 performs fracture determination of the extracted fracture determination target portion (S39), records the fracture determination, and finishes the fracture determination.

In the second fracture determination mode, subsequent to the deformation analysis after the predetermined step interval from the start of deformation of the metal structure, an arbitrary or predetermined fracture determination target portion is extracted from the deformation state thereof, and fracture determination is performed for the extracted fracture determination target portion. This processing is performed until the end of deformation. Therefore, fracture determination is possible when the fracture determination target portion of the metal structure is in either of an elastic state and a plastic state. Further, since fracture determination of a fracture determination target portion can be performed sequentially, the user can comprehend what process the metal structure gets through to fracture.

Thus, the fracture determination apparatus 10 can perform fracture determination of a deformation state which the user desires. Further, since the fracture determination apparatus 10 is capable of performing fracture determination sequentially after the end of deformation of the metal structure or from the start of deformation to the end of deformation of the metal structure, it is possible to respond flexibly to an arbitrary fracture determination method which the user desires.

First Embodiment

Next, a fracture determination method according to a first embodiment will be described. Note that although fracture determination of one fracture determination target portion extracted by the extraction unit 5 will be described below, the fracture determination is performed similarly for any other extracted fracture determination target portion.

The fracture analyzing unit 6 is capable of performing fracture determination of a fracture determination target portion in a process including one or more deformation path variations. The fracture analyzing unit 6 includes the estimation unit 7, the conversion unit 8, and the fracture determination unit 9 as described above. The estimation unit 7 estimates a fracture limit line in a strain space via a proportional loading path. The conversion unit 8 converts the fracture limit line in the strain space obtained via the proportional loading path into a fracture limit line in a stress space (hereinafter referred to as a fracture limit stress line). The fracture determination unit 9 calculates a fracture risk using the fracture limit stress line, performs fracture determination from the calculated fracture risk, and displays the result of the fracture determination on the display unit 3, and/or displays the fracture risk in the form of contour lines.

Figure 4:
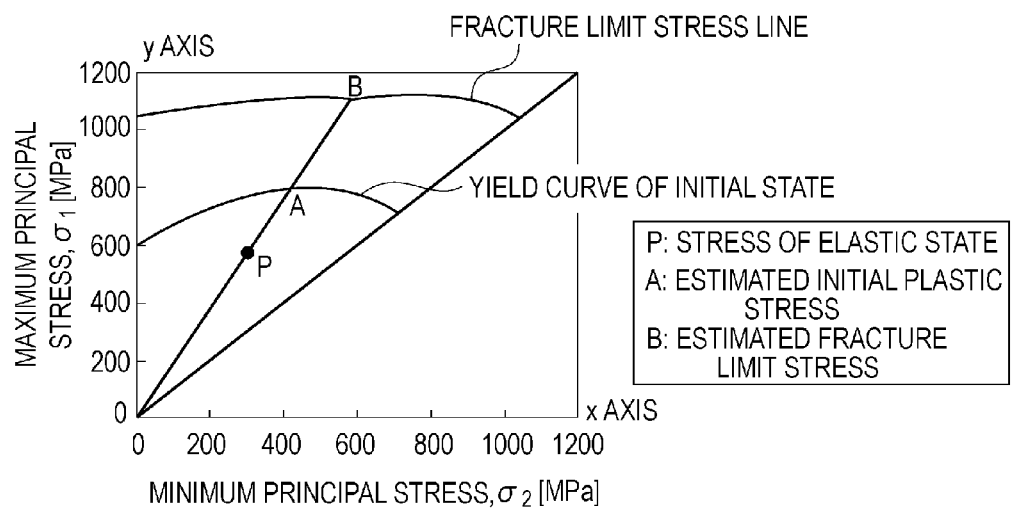
FIG. 4 is a diagram illustrating a stress space in an elastic state.
Figure 5:
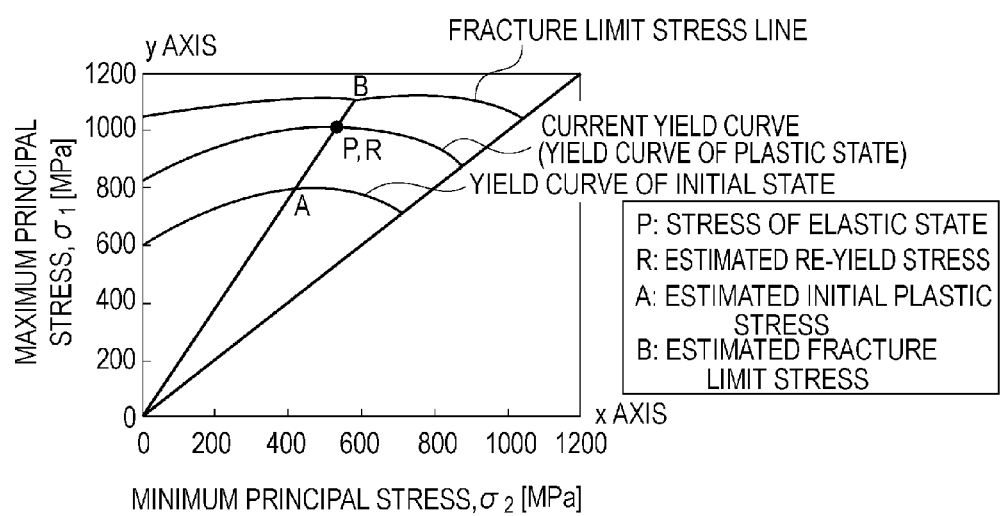
FIG. 5 is a diagram illustrating a stress space in a plastic state.
Figure 6:
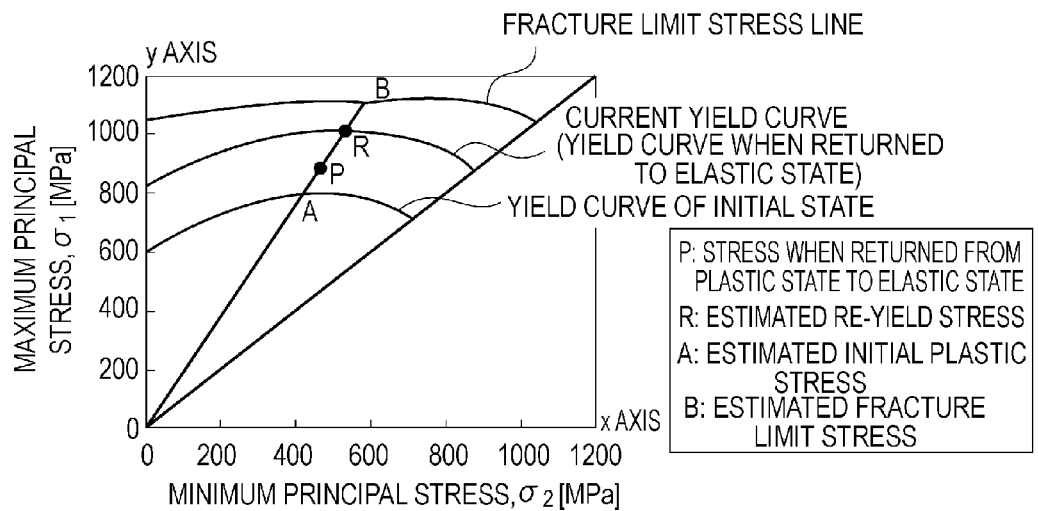
FIG. 6 is a diagram illustrating a stress space when returned from the plastic state to the elastic state.

Here, fracture limit stress lines converted into a stress space by the conversion unit 8 are illustrated in FIG. 4 to FIG. 6. FIG. 4 to FIG. 6 are diagrams illustrating the stress space on a (x, y) coordinate plane. In FIG. 4 to FIG. 6, the extracted fracture determination target portion is the same, but the timing of extraction differs. That is, FIG. 4 illustrates the stress space at the time the elastic state before the fracture determination target portion starts to plastically deform is extracted. FIG. 5 illustrates the stress space at the time the plastic state when the fracture determination target portion starts to plastically deform is extracted. FIG. 6 illustrates the stress space at the time the state when the fracture determination target portion has returned from the plastic state to the elastic state is extracted. Hereinafter, FIG. 4 to FIG. 6 will be described specifically.

In the stress space of the elastic state illustrated in FIG. 4, the above-described fracture limit stress line can be depicted on the outermost side, and on the inside thereof, a yield curve of an initial state estimated based on the material of the metal structure can be depicted. Further, a stress P of the elastic state illustrated in FIG. 4 is one occurring in the fracture determination target portion, and can be represented with a minimum principal stress $\sigma 2$ on the x axis and a maximum principal stress $\sigma 1$ on the y axis.

In FIG. 4, assuming that the stress P goes through the proportional loading path, a straight line satisfying a relation $y=(\sigma 1/\sigma 2)x$ connecting the origin and the stress P can be obtained. The intersection where this straight line satisfying the relation $y=(\sigma 1/\sigma 2)x$ and the yield curve of the initial state cross each other is an estimated initial plastic stress A. The initial plastic stress A is a stress when the fracture determination target portion changes from the elastic state to the plastic state. Therefore, it is in the elastic state until the stress P exceeds the initial plastic stress A in the fracture determination target portion, and when the stress exceeds the initial plastic stress A, the portion starts to plastically deform and turns to the plastic state.

Further, in FIG. 4, the intersection where the above-described straight line satisfying the relation $y=(\sigma 1/\sigma 2)x$ and the fracture limit stress line cross each other is an estimated fracture limit stress B. The fracture limit stress B is a stress when the fracture determination target portion fractures. Therefore, a fracture occurs when the stress P in the fracture determination target portion reaches the fracture limit stress B.

Next, in the stress space of the plastic state illustrated in FIG. 5, the same fracture limit stress line and yield curve of the initial state as in FIG. 4 can be depicted. Further, a stress P of the plastic state illustrated in FIG. 5 is one occurring in the fracture determination target portion, and can be represented with a minimum principal stress $\sigma 2$ on the x axis, and a maximum principal stress $\sigma 1$ on the y axis.

In FIG. 5, as described above in FIG. 4, the stress P has exceeded the initial plastic stress A, and hence the fracture determination target portion is in the plastic state. Further, in conjunction with increase of the stress P of the plastic state, the yield curve of the plastic state can be illustrated.

Now, in the deformation analysis, the fracture determination target portion may be unloaded due to, for example, buckling of a different portion from the fracture determination target portion, or the like. At this time, the stress P of the fracture determination target portion is smaller than the stress P of the plastic state, and thus the fracture determination target portion returns from the plastic state to the elastic state. FIG. 6 illustrates the stress space when the fracture determination target portion has returned from the plastic state to the elastic state in this manner.

In the stress space when the portion has returned from the plastic state to the elastic state as illustrated in FIG. 6, the same fracture limit stress line and yield curve of the initial state as in FIG. 4 can be depicted. Further, a stress P when the portion returned to the elastic state illustrated in FIG. 6 is one occurring in the fracture determination target portion, and can be represented with a minimum principal stress $\sigma 2$ on the x axis, and a maximum principal stress $\sigma 1$ on the y axis. Note that the stress P is smaller than the stress P of the plastic state illustrated in FIG. 5 due to the unloading.

Further, in FIG. 6, a yield curve when the portion returned to the elastic state can be illustrated. The yield curve when the portion returned to the elastic state and the yield curve of the plastic state illustrated in FIG. 5 are the same curve. Hereinafter, the yield curve when the portion returned to the elastic state of FIG. 6 and the yield curve when the portion returned to the elastic state of FIG. 5 are described as a current yield curve. That is, when the fracture determination target portion has returned from the plastic state to the elastic state, the current yield curve illustrated in FIG. 6 is maintained unchanged from the current yield curve illustrated in FIG. 5. Therefore, the current yield curve illustrated in FIG. 6 can be obtained from the current yield curve illustrated in FIG. 5. Here, the portion is in the elastic state when the stress P when the portion returned to the elastic state is located inside the current yield curve as illustrated in FIG. 6. On the other hand, from the state illustrated in FIG. 6, when the stress P of the fracture determination target portion exceeds the current yield curve, the portion starts to plastically deform again and turns to the plastic state. From this, the intersection where the straight line satisfying the relation y=(σ1/σ2)x and the current yield curve is an estimated re-yield stress R where the fracture determination target portion starts to plastically deform again.

Now, when fracture determination is performed using the stress space illustrated in FIG. 4 to FIG. 6, the fracture risk (or deformation margin) has been calculated hitherto by comparing the fracture limit stress line with the stress P occurring in the fracture determination target portion. Specifically, the stress degree has been calculated with the following expression $f_1$.

Comparative example:

$$f_1 = \frac{\overline{OP}}{\overline{OB}} \quad \text{[Expression 1]}$$

This expression $f_1$ represents the fracture risk as the ratio between the distance to the coordinate point of the stress P occurring in the fracture determination target portion in each of FIG. 4 to FIG. 6 and the distance to the coordinate point of the fracture limit stress B, from the origin as a reference where there is zero stress which is illustrated in FIG. 4 to FIG. 6.

With the expression $f_1$, when the stress P of the plastic state and the re-yield stress R match as in the plastic state illustrated in FIG. 5, the fracture risk which is accurate to a certain degree can be calculated. However, when the portion has returned from the plastic state to the elastic state as illustrated in FIG. 6, the stress P when the portion returned to the elastic state becomes closer to the origin than the re-yield stress R. Accordingly, despite that the plasticity of the fracture determination target portion is proceeding, the fracture risk is calculated smaller than the re-yield stress R, and it is not possible to perform the accurate fracture determination. Further, with the expression $f_1$, since the reference for calculating the fracture risk is the origin, the stress P of the elastic state illustrated in FIG. 4 does not exceed the initial plastic stress A in the elastic state, and the fracture risk is calculated despite that no fracture risk occurs.

Accordingly, in this embodiment, when fracture determination of the fracture determination target portion is performed, in the plastic state illustrated in FIG. 5, the fracture risk is calculated using the stress P of the plastic state. Further, when the portion has returned from the plastic state to the elastic state as illustrated in FIG. 6, the re-yield stress R is used instead of the stress P when the portion returned to the elastic state, so as to calculate the fracture risk.

Moreover, to calculate the fracture risk excluding the case where no fracture risk occurs, the reference for calculating the fracture risk is set to the initial plastic stress A instead of the origin. Therefore, in the elastic state illustrated in FIG. 4, the fracture risk is calculated as 0.

Specifically, the fracture risk is calculated with the following expression $f_2$.

The present invention example:

When in the elastic state $f_2 = 0$ [Expression 2]

When in the plastic state $f_2 = \dfrac{\overline{AP}}{\overline{AB}}$

When returned from the plastic state to the elastic state $f_2 = \dfrac{\overline{AR}}{\overline{AB}}$ When the above-described expression $f_2$ is used, in the elastic state illustrated in FIG. 4, the fracture risk is calculated as 0. Further, in the plastic state illustrated in FIG. 5, the fracture risk is calculated as a numeric value between 0 and 1 based on the coordinate point of the stress P of the plastic state. Further, when the portion has returned from the plastic state to the elastic state as illustrated in FIG. 6, the fracture risk is calculated as a numeric value between 0 and 1 based on the coordinate point of the re-yield stress R.

Next, the fracture determination unit 9 can perform fracture determination using the calculated fracture risk as a fracture determination index. Specifically, the fracture determination unit 9 performs fracture determination based on a safety coefficient which is inputted in advance by the user via the input unit 2. The fracture determination unit 9 determines that "there is no possibility of fracture" when the fracture risk is 0, determines that "risk of fracture is low" when the fracture risk is larger than 0 and smaller than the safety coefficient, determines that "risk of fracture is high" when the fracture risk is larger than the safety coefficient and smaller than 1, or determines that "fracture occurred" when the fracture risk is 1. The safety coefficient can be set arbitrarily by the user in the range of, for example, 0 to 1, such as 0.9.

Figure 7:
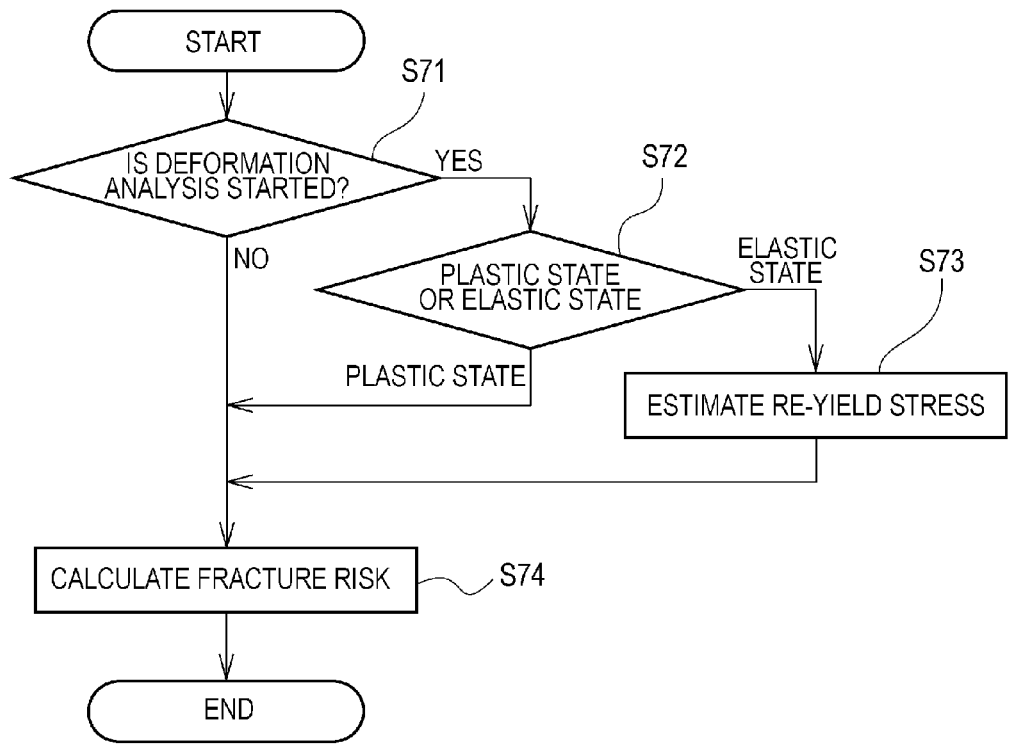
FIG. 7 is a flowchart illustrating processing of calculating a fracture risk.

Next, a method for calculating the above-described fracture risk will be described with reference to the flowchart illustrated in FIG. 7. Here, the estimation unit 7 already estimated the fracture limit line in the strain space, and the conversion unit 8 converts the estimated fracture limit line in the strain space into the fracture limit stress line in the stress space and presents it on a (x, y) coordinate plane as illustrated in FIG. 4 to FIG. 6. Similarly, the conversion unit 8 illustrates the yield curve of an initial state and, in some cases, the current yield curve illustrated in FIG. 5 and FIG. 6 on the (x, y) coordinate plane.

First, the fracture determination unit 9 determines whether the fracture determination target portion has started to plastically deform or not (S71). The fracture determination unit 9 may determine that the portion has started to plastically deform when a plastic strain is stored during deformation analysis by the deformation analyzing unit 4.

When the fracture determination target portion has started to plastically deform, the fracture determination unit 9 determines whether the fracture determination target portion is in a plastic state or in a state returned from the plastic state to an elastic state (S72). The fracture determination unit 9 determines that it is in the plastic state when the stress P has reached the current yield curve in the stress space illustrated in FIG. 5 and FIG. 6, or determines that it is in the state returned from the plastic state to an elastic state when the stress P has not reached the current yield curve.

Figure 2:
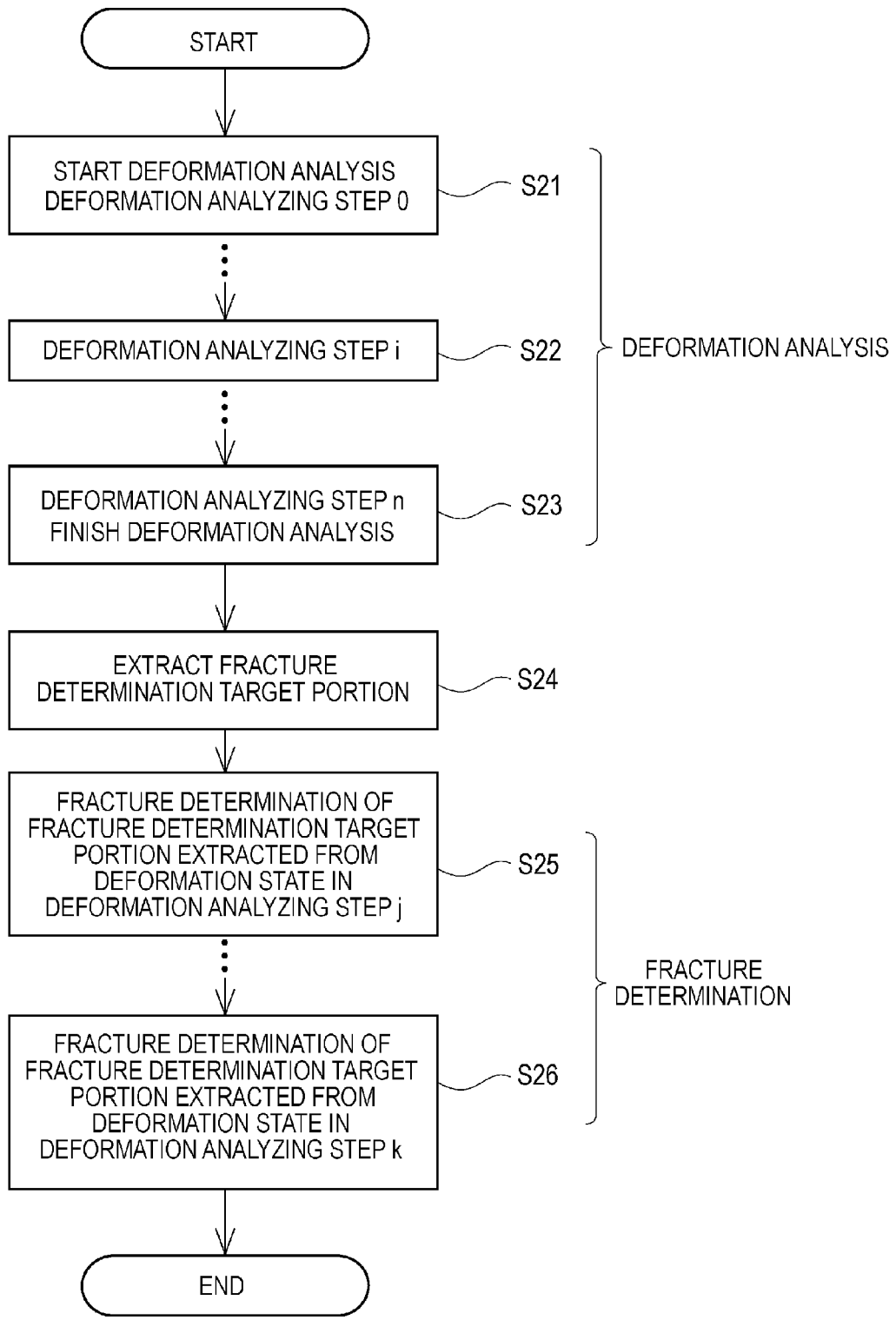
FIG. 2 is a flowchart illustrating processing of a fracture determination method in a first fracture determination mode.
Figure 3:
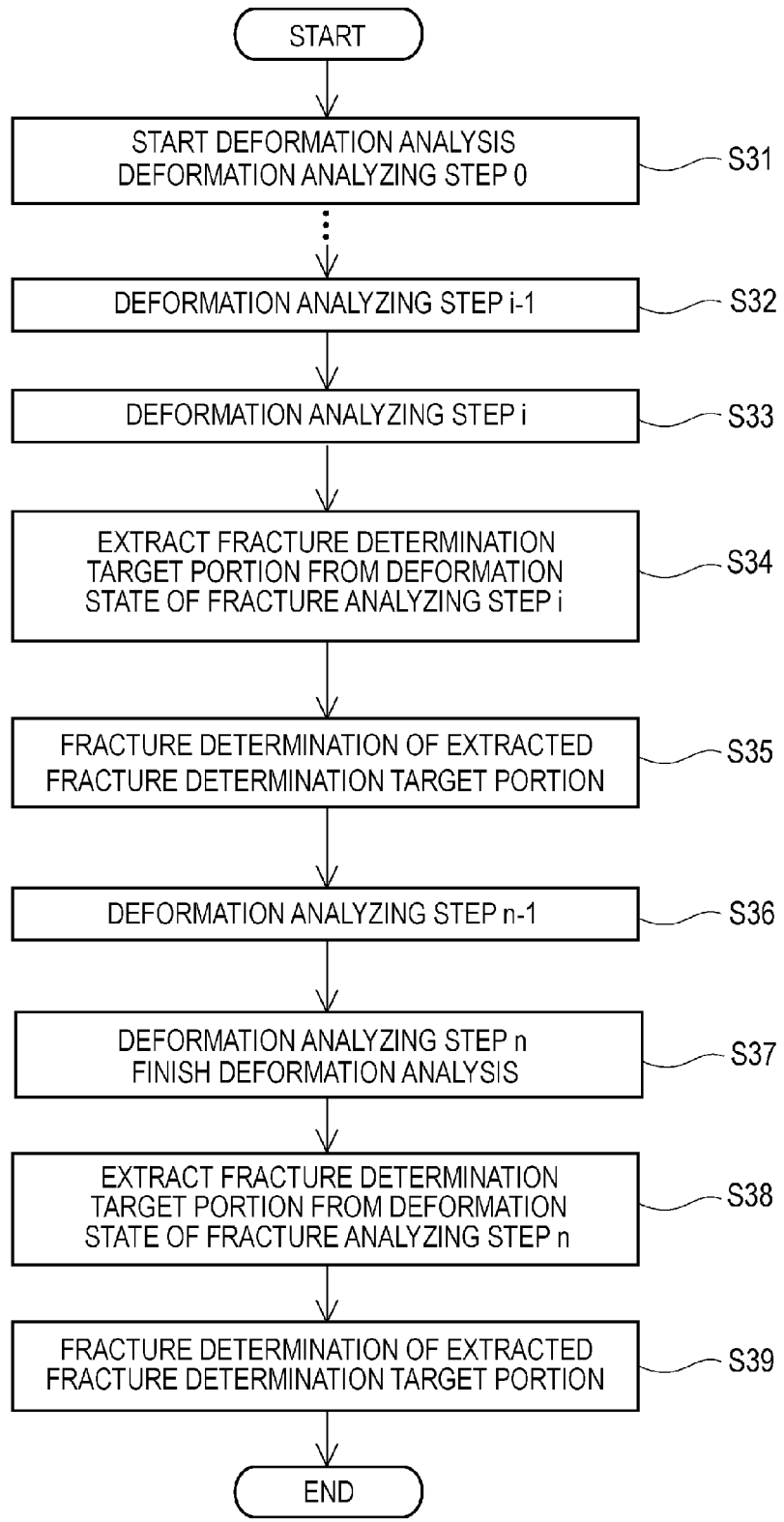
FIG. 3 is a flowchart illustrating processing of a fracture determination method in a second fracture determination mode.

Note that in the above-described process of deformation analysis illustrated in FIG. 2 and FIG. 3, the deformation analyzing unit 4 stores a plastic strain of the fracture determination target portion, and the estimation unit 7 and the conversion unit 8 use this plastic strain to depict the current yield curve on the (x, y) coordinate plane. This processing is similar to the processing of the conversion unit 8 to convert the fracture limit line in the strain space estimated by the estimation unit 7 into the fracture limit stress line, and depict this on the (x, y) coordinate plane.

In the case where the fracture determination target portion is in a state returned from the plastic state to the elastic state, the fracture determination unit 9 estimates the re-yield stress R (S73). Specifically, as described above with FIG. 6, the fracture determination unit 9 calculates as the re-yield stress R the intersection where the straight line satisfying the relation y=(σ1/σ2)x and the current yield curve cross each other.

Next, the fracture determination unit 9 calculates the fracture risk of the fracture determination target portion (S74). When it is determined that the fracture determination target portion is before starting to plastically deform (when proceeding to NO from S71), the fracture determination unit 9 determines that the fracture determination target portion is in an elastic state, and calculates the fracture risk as 0 with the above-described expression $f_2$.

Further, when the fracture determination target portion is in a plastic state (when proceeding to plastic state from S72), the fracture determination unit 9 calculates the fracture risk using the stress P of the plastic state, the initial plastic stress A, and the fracture limit stress B in the above-described expression $f_2$. Note that as described above with FIG. 5, the fracture determination unit 9 calculates as the initial plastic stress A the intersection where the straight line satisfying the relation y=(σ1/σ2)x and the yield curve of the initial state cross each other. Further, the fracture determination unit 9 calculates as the fracture limit stress B the intersection where the straight line satisfying the relation y=(σ1/σ2)x and the fracture limit stress line cross each other.

When the fracture determination target portion has returned from the plastic state to the elastic state (when proceeding from S73 to S74), the fracture determination unit 9 calculates the fracture risk using the re-yield stress R estimated in step S73, the initial plastic stress A, and the fracture limit stress B in the above-described expression $f_2$. Note that the initial plastic stress A and the fracture limit stress B can be calculated similarly to the case of the plastic state.

Thus, the fracture determination unit 9 calculates the fracture risk using the re-yield stress R when the fracture determination target portion has returned from a plastic state to an elastic state. Therefore, when fracture determination is performed in the stress space, it is possible to avoid a problem that the fracture risk changes when the fracture determination target portion has returned from the plastic state to the elastic state.

Further, by setting the reference for calculating the fracture risk to the initial plastic stress A instead of the origin, the fracture risk can be calculated excluding the case where no fracture risk occurs.

Note that although the above-described fracture determination method is described from a state that no plastic deformation has occurred in the fracture determination target portion, it is possible to perform fracture determination similarly also when a plastic deformation has occurred in part of the metal structure. That is, the fracture determination apparatus 10 can perform fracture determination also on a metal structure on which stamping or the like for example is performed and a plastic deformation has occurred.

In the case of such a metal structure, depending on the fracture determination target portion, the current yield curve exists outside the yield curve of the initial state as illustrated in FIG. 6 before the deformation analysis is started. By the deformation analyzing unit 4 using a plastic strain stored in the deformation analysis of stamping or the like, the conversion unit 8 can depict this current yield curve on the (x, y) coordinate plane of the stress space.

Second Embodiment

Next, a fracture determination method according to a second embodiment will be described with reference to FIG. 8.

Figure 8:
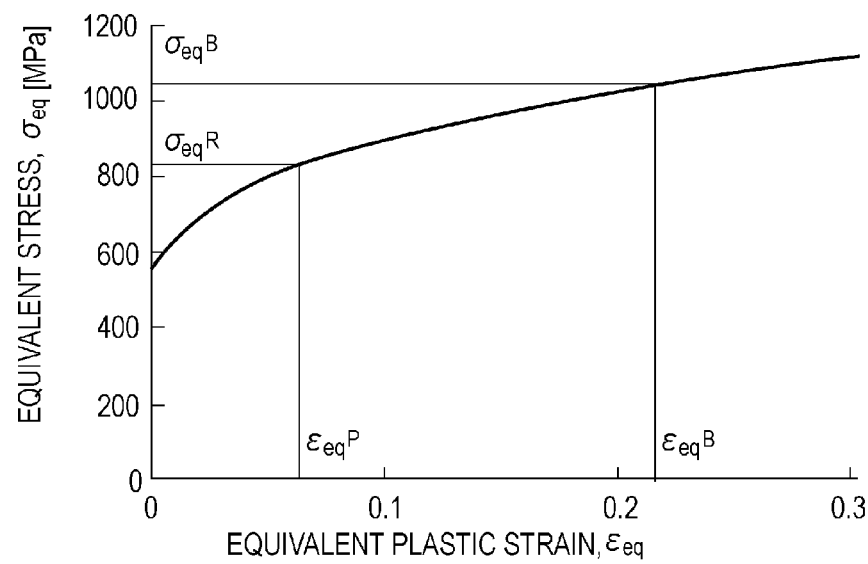
FIG. 8 is a diagram illustrating processing of calculating an equivalent plastic strain and a fracture limit equivalent plastic strain.

In the second embodiment, the fracture determination unit 9 converts each of the re-yield stress R and the fracture limit stress B which are calculated using the stress space in the first embodiment into an equivalent stress, and an equivalent stress-equivalent plastic strain curve illustrated in FIG. 8 is used to obtain an equivalent plastic strain $\epsilon_{eq}^P$ and a fracture limit equivalent plastic strain $\epsilon_{eq}^B$, so as to calculate the fracture risk. The equivalent stress-equivalent plastic strain curve illustrated in FIG. 8 is based on the material of the metal structure, and is stored in advance in the fracture determination apparatus 10. Further, similarly to the first embodiment, for the elastic state until the stress P of the fracture determination target portion exceeds the initial plastic stress A, the fracture risk is calculated as 0.

Specifically, in the plastic state illustrated in FIG. 5, the fracture determination unit 9 calculates the stress P of the plastic state as the re-yield stress R. Further, the fracture determination unit 9 calculates the fracture limit stress B from the intersection where the straight line satisfying the relation y=(σ1/σ2)x and the fracture limit stress line cross each other.

Further, when the portion has returned from the plastic state to the elastic state as illustrated in FIG. 6, the fracture determination unit 9 calculates the re-yield stress R from the intersection where the straight line satisfying the relation y=(σ1/σ2)x and the current yield curve cross each other. Moreover, the fracture determination unit 9 calculates the fracture limit stress B from the intersection where the straight line satisfying the relation y=(σ1/σ2)x and the fracture limit stress line cross each other.

The fracture determination unit 9 converts each of the calculated re-yield stress R and the fracture limit stress B into an equivalent stress, and uses the equivalent stress-equivalent plastic strain curve illustrated in FIG. 8 to obtain the equivalent plastic strain $\epsilon_{eq}^P$ and the fracture limit equivalent plastic strain $\epsilon_{eq}^B$. Here, the re-yield stress R is the same either in the plastic state illustrated in FIG. 5 or when the portion has returned from the plastic state to the elastic state as illustrated in FIG. 6, and also the fracture limit stress B is the same. Accordingly, the obtained equivalent plastic strain $\epsilon_{eq}^P$ is the same, and the fracture limit equivalent plastic strain $\epsilon_{eq}^B$ is the same as well. The fracture determination unit 9 substitutes the obtained equivalent plastic strain $\epsilon_{eq}^P$ and fracture limit equivalent plastic strain $\epsilon_{eq}^B$ in the following expression $f_3$ to calculate the fracture risk.

The present invention example: [Expression 3]

When in the elastic state $f_3 = 0$

When in the plastic state and when returned from the plastic state to the elastic state $$f_3 = \frac{\varepsilon_{eq}^P}{\varepsilon_{eq}^B}$$

In the equivalent stress-equivalent plastic strain curve illustrated in FIG. 8, the amount of change of the equivalent plastic strain is large relative to the amount of change of the equivalent stress, and thus using the equivalent plastic strain and the fracture limit equivalent plastic strain to calculate the fracture risk improves its accuracy. Further, it is possible to suppress deviation of the fracture risk viewed through stress from the fracture risk viewed through strain due to the non-linearity of stress and strain.

Incidentally, similarly to the first embodiment, the fracture determination unit 9 can perform fracture determination using the calculated fracture risk and safety factor.

Third Embodiment

Next, a fracture determination method according to a third embodiment will be described.

In the third embodiment, the fracture risk described in the first embodiment or the second embodiment is calculated and, irrespective of whether the fracture determination target portion is in an elastic state or plastic state or has returned from the plastic state to the elastic state as illustrated in FIG. 4 to FIG. 6, the stress P occurring in the fracture determination target portion and the fracture limit stress B are used in the above-described comparative example $f_1$ to calculate the fracture risk. In this case, the fracture determination unit 9 displays at least one of the fracture risk calculated by the method of the first embodiment or the second embodiment and the fracture risk calculated by the comparative example on the display unit 3 in response to an instruction by the user via the input unit 2.

Specifically, the fracture determination unit 9 calculates as the fracture risk the ratio between the distance to the coordinate point of the stress P occurring in the fracture determination target portion in FIG. 4 to FIG. 6 and the distance to the coordinate point of the fracture limit stress B, with reference to the origin where there is zero stress. Note that the fracture determination unit 9 calculates the fracture limit stress B from the intersection where the straight line satisfying the relation $y=(\sigma1/\sigma2)x$ and the fracture limit stress line cross each other.

When the user has an intention of increasing the margin of a material used for the fracture determination target portion, or the like, the fracture risk calculated by the first embodiment or the second embodiment will be a more beneficial index. On the other hand, when the user has an intention of suppressing stress in the fracture determination target portion, or the like, it may be desired to comprehend stress occurring in the fracture determination target portion regardless of the state of the fracture determination target portion. In this case, the fracture risk calculated by the above-described comparative example $f_1$ will be a more beneficial index. Therefore, by calculating both the fracture risk by the method of the first embodiment or the second embodiment and the fracture risk by the method of the comparative example, one of them can be selected and used depending on the intention such as 1) increasing the margin as a material, and 2) suppressing stress. That is, it becomes possible to design the metal structure by making a selection between securing the margin as a material and securing the margin as a stress state.

Next, a specific calculation method by the above-described estimation unit 7, conversion unit 8, and fracture determination unit 9 will be described.

The estimation unit 7 uses, for example, an approximate expression of stress-strain curve obtained from a uniaxial tensile test, $$\sigma_{eq} = (\varepsilon_{eq} + \varepsilon_0)^n \text{ or } \sigma_{eq} = C\varepsilon_{eq}^n, \quad [\text{Expression 4}]$$

a localized necking model $$\varepsilon_1^* = \frac{n}{1+\rho}\left(\rho = \frac{d\varepsilon_2}{d\varepsilon_1} < 0\right), \text{ and} \quad [\text{Expression 5}]$$

a diffused necking model $$\varepsilon_1^* = \frac{2n(\rho^2 + \rho + 1)}{(\rho + 1)(2\rho^2 - \rho + 2)}(\rho \geq 0) \quad [\text{Expression 6}]$$

together to obtain a necking occurrence limit in a strain space, so as to estimate the fracture limit line in a strain space via a proportional loading path.

The estimation unit 7 may use an approximate expression of stress-strain curve obtained from a uniaxial tensile test, $$\sigma_{eq}=(\epsilon_{eq}+\epsilon_0)^n \text{ or } \sigma_{eq}=C\epsilon_{eq}^n, \quad [\text{Expression 7}]$$

a constitutive equation in which the direction of a plastic strain increment tensor depends on a stress increment tensor as a plastic strain increment rule, a material parameter Kc defining the direction of the plastic strain increment tensor, and a Storen-Rice localized necking model so as to obtain a necking occurrence limit in the strain space, and estimate the fracture limit line in the strain space via a proportional loading path. Here, the estimation unit 7 identifies the material parameter Kc based on measurement values of one or more maximum fracture limit strains $\epsilon_1$ and minimum fracture limit strains $\epsilon_2$.

Note that in this example, the case of logically estimating the fracture limit line in the strain space using the estimation unit 7 is illustrated, but the fracture limit line in the strain space may be measured experimentally without using the estimation unit 7. Specifically, after obtaining plural in-plane strain ratios with respect to a metal sheet by a proportional loading experiment, the fracture limit line in the strain space is obtained using measurement values of the maximum fracture limit strain $\epsilon_1$ and the minimum fracture limit strain $\epsilon_2$ in each of the strain ratios.

When converting the fracture limit line in the strain space into the fracture limit stress line in the stress space, the conversion unit 8 performs the above-described conversion using a vertical rule of yield surface as a plastic strain increment rule. Specifically, a Mises yield function which is a relational expression of an equivalent plastic strain $\epsilon_{eq}$ and each strain component $\epsilon_{ij}$, $$\varepsilon_{eq} = \sqrt{\frac{2}{3}\varepsilon_{ij}\varepsilon_{ij}} \text{ , is used as described above.} \quad [\text{Expression 8}]$$

The fracture determination unit 9 performs evaluation by comparing the positional relation between the fracture limit stress line in the stress space converted by the conversion unit 8 and the strain state of each portion obtained from simulation results by a finite element method in a plastic deformation process, and determines that "fracture occurred", "risk of fracture is high", or the like when the strain in the deformation process reaches this limit strain. Here, using a dynamic explicit method which is one of finite element methods as a method of deformation analysis, the plastic strain obtained by the dynamic explicit method is converted into a stress, and this stress and the fracture limit stress line in the stress space are compared.

Note that the fracture determination unit 9 may convert a strain obtained from a deformation state of the metal structure evaluated by experiment into a stress, and quantitatively evaluate the presence/absence of occurrence of fracture using the fracture limit stress line in the stress space, instead of performing the above-described simulation.

Here, when a fast deformation occurs in the metal structure in a collision analysis of an automotive member, the fracture determination unit 9 executes the deformation analysis considering the strain rate dependence of the deformation stress of the metal structure. The fracture determination unit 9 converts a plastic strain obtained from this deformation analysis to calculate a stress at a reference strain rate, and compares this stress with the fracture limit stress line in the stress space corresponding to this reference strain rate.

Figure 9:
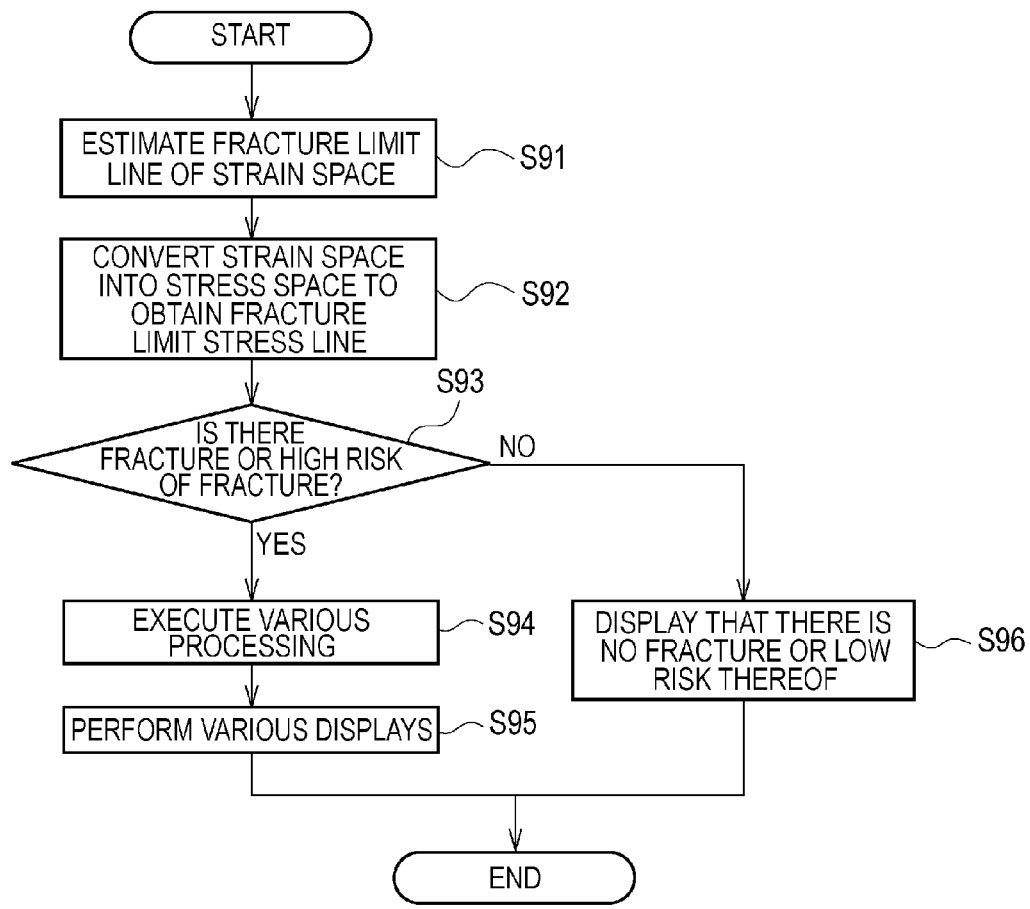
FIG. 9 is a flowchart illustrating fracture determination in a formation process.

Next, the processing of performing fracture determination in S25, S26 illustrated in FIG. 2 and S35, S39 illustrated in FIG. 3 which are described above will be described with reference to a flowchart illustrated in FIG. 9. FIG. 9 is a flowchart for performing fracture determination in the formation process of a metal structure, specifically a metal sheet.

First, the estimation unit 7 estimates the fracture limit line in the strain space via a proportional loading path based on the material and mechanical characteristic values (t (thickness of metal sheet), YP (yield strength), TS (tensile strength), El (total elongation), U. El (uniform elongation), r value (Lankford value), n-th power hardening law/Swift hardening law) of the metal sheet which are stored in advance (S91).

Subsequently, the conversion unit 8 converts, using the yield function of Mises for example, the fracture limit line in the strain space which is measured experimentally into the fracture limit stress line in the stress space (S92).

Subsequently, the fracture determination unit 9 uses the fracture limit stress line converted by the conversion unit 8, the stress occurring in the fracture determination target portion, the current yield curve, and the yield curve of an initial state to calculate the fracture risk of the fracture determination target portion, and performs fracture determination (S93). In the fracture determination, using the fracture risk and the safety factor as described above, a determination such as "there is no possibility of occurrence of fracture", "risk of fracture is low", "risk of fracture is high", "fracture occurred", or the like is made. Further, the processing of calculating the fracture risk is equivalent to the above-described flowchart illustrated in FIG. 7.

In step S93, when it is determined that the "fracture occurred" or "risk of fracture is high" using the fracture risk of the fracture determination target portion and the safety factor, the fracture determination unit 9 performs the following various processing (S94).

That is, the fracture determination unit 9 outputs the element ID, sheet thickness of metal sheet, strain, and stress information to a log file. In some cases, the fracture determination unit 9 deletes the fractured element, and the deformation analyzing unit 4 continues the deformation analysis after the fracture.

Subsequently, the fracture determination unit 9 performs the following various displays on the display unit 3 (step S95). Specifically, the fracture determination unit 9 contour displays the fracture risk that a fracture occurs in the metal sheet by a scalar value, or displays the stress histories and fracture limit stress line of the fracture risk portion in the stress space. Simultaneously, the fracture determination unit 9 contour displays the risk of occurrence of a wrinkle in the metal sheet. Here, the risk of fracture may be displayed with respect to dispersion (average value, lower limit value) within the standard of shipping test values.

On the other hand, in step S93, when it is determined that "there is no possibility of occurrence of fracture" or "risk of fracture is low" in each fracture determination target portion, the fracture determination unit 9 displays this information on the display unit 3 (S96).

Figure 10:
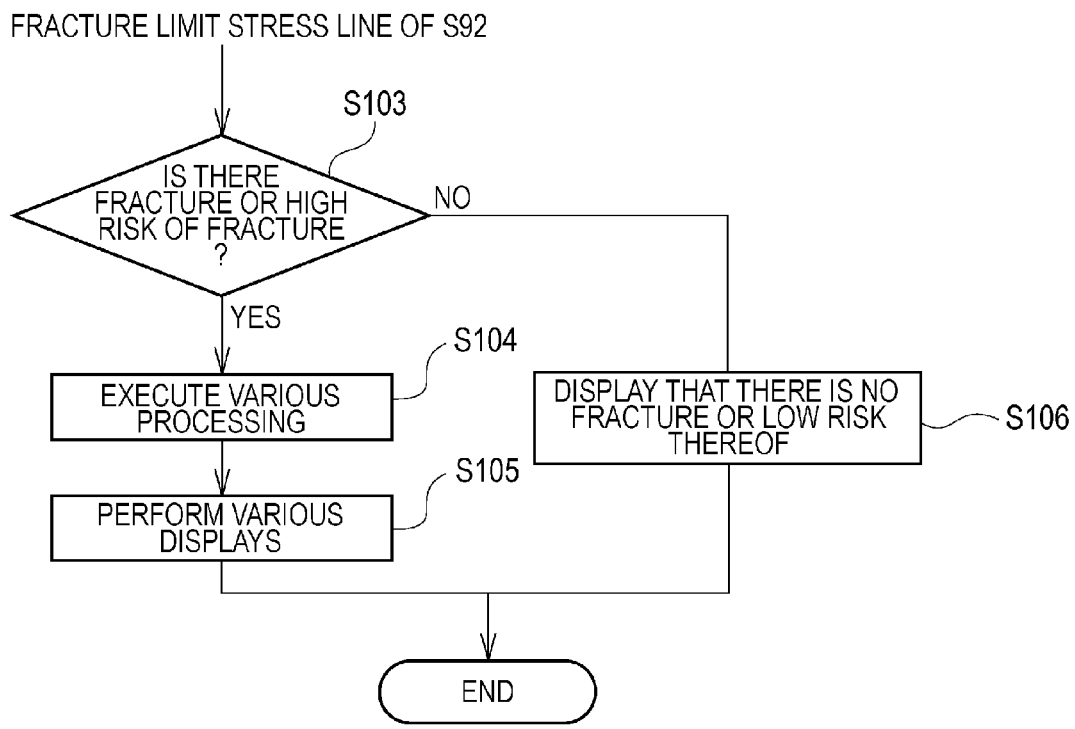
FIG. 10 is a flowchart illustrating fracture determination in a collision process.

FIG. 10 is a flowchart of the case where fracture determination is performed in a collision process of the structure formed of the metal sheet by subjecting the metal sheet to the formation process, subsequent to the fracture determination in the formation process of the metal sheet of FIG. 9.

In this case, the fracture limit stress line converted in step S92 of FIG. 9 is inherited and used. The fracture determination unit 9 carries out the deformation analysis in consideration of strain rate dependence of a deformation stress in the structure formed of the metal sheet. The fracture determination unit 9 converts a plastic strain obtained from this deformation analysis to calculate the stress at a reference strain rate, compares this stress with the fracture limit stress line corresponding to the reference strain rate, calculates the fracture risk of the fracture determination target portion, and performs fracture determination (S103). In the fracture determination, using the fracture risk and the safety factor as described above, a determination such as "there is no possibility of occurrence of fracture", "risk of fracture is low", "risk of fracture is high", "fracture occurred", or the like is made. Further, the processing of calculating the fracture risk is equivalent to the above-described flowchart illustrated in FIG. 7.

In this step S103, the fracture determination unit 9 inherits the deformation state of the metal sheet subjected to the deformation analysis in the formation process of FIG. 9 as an initial condition of the deformation analysis in the collision process. This deformation state is a sheet thickness and an equivalent plastic strain of the metal sheet, or a sheet thickness, an equivalent plastic strain, and a stress tensor and a strain tensor of the metal sheet.

In step S103, when it is determined that the "fracture occurred" or "risk of fracture is high" using the fracture risk of the fracture determination target portion and the safety factor, the fracture determination unit 9 performs the following various processing (S104).

That is, the fracture determination unit 9 outputs the element ID, sheet thickness of metal sheet, strain, and stress information to a log file. In some cases, the fracture determination unit 9 deletes the fractured element, and the deformation analyzing unit 4 continues the deformation analysis after the fracture.

Subsequently, the fracture determination unit 9 performs the following various displays on the display unit 3 (step S105). Specifically, the fracture determination unit 9 contour displays the fracture risk that a fracture occurs in the structure formed of the metal sheet by a scalar value, or displays the stress histories and fracture limit stress line of the fracture risk portion in the stress space. Simultaneously, the fracture determination unit 9 contour displays the risk of occurrence of a wrinkle in the structure formed of the metal sheet. Here, the risk of fracture may be displayed with respect to dispersion (average value, lower limit value) within the standard of shipping test values.

On the other hand, in step S103, when it is determined that "there is no possibility of occurrence of fracture" or "risk of fracture is low" in each fracture determination target portion, the fracture determination unit 9 displays this information on the display unit 3 (S106).

As described above, according to this embodiment, when fracture determination of the metal structure is performed, it is possible to easily and efficiently obtain the fracture limit stress line and perform fracture determination with high accuracy. Thus, it is possible to quantitatively evaluate the risk of fracture at the time of stamping or collision, and efficient and precise design of an automobile body or the like considering the material, construction method, and structure simultaneously can be achieved.

The functions of respective components (excluding the display unit 3 and the input unit 2) forming the above-described fracture determination apparatus 10 can be achieved by operation of a program stored in a RAM, ROM, or the like of a computer. Similarly, the respective steps of deformation analysis and fracture determination (flowcharts of FIG. 2, FIG. 3, FIG. 7, FIG. 9, and FIG. 10) can be achieved by operation of a program stored in a RAM, ROM, or the like of a computer. This program and a computer readable storage medium recording this program are included in the present invention.

Specifically, the program is provided to the computer by, for example, recording in a recording medium such as CD-ROM, or via one of various types of transmission media. As the recording medium recording the program, a flexible disk, a hard disk, a magnetic tape, an optical disk, a non-volatile memory card, or the like can be used besides the CD-ROM. Oh the other hand, as the transmission medium for the program, a communication medium in a computer network system for supplying program information by propagating as carrier waves can be used. Here, the computer network is LAN, WAN such as the Internet, radio communication network, or the like, and the communication medium is a wired line of optic fiber or the like, a wireless line, or the like.

Further, the program included in the present invention is not only one such that a supplied program is executed in a computer to achieve the functions of the above-described embodiments. For example, when this program cooperates with the OS (operating system) operating in the computer or with other application software or the like to achieve the functions of the above-described embodiments, such a program is included in the present invention. Further, when all or part of processing of the supplied program is run on a function expansion board or function expansion unit of the computer to achieve the functions of the above-described embodiments, such a program is included in the present invention.

Figure 11:
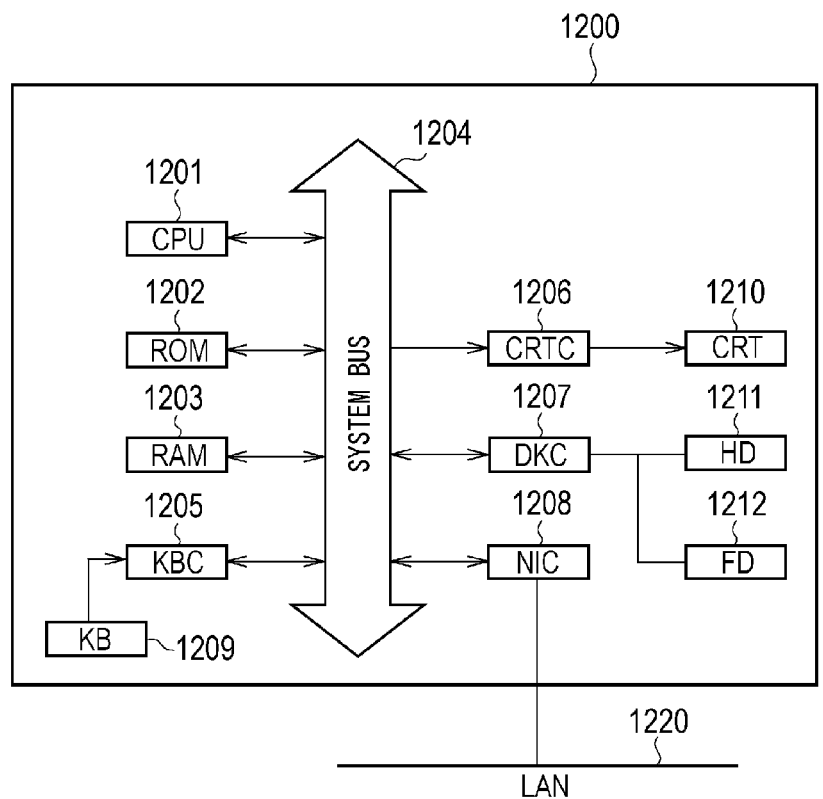
FIG. 11 is a schematic diagram illustrating an internal structure of the fracture determination apparatus.

For example, FIG. 11 is a schematic diagram illustrating an internal structure of the fracture determination apparatus 10. In FIG. 11, numeral 1200 denotes a personal computer (PC) including a CPU 1201. The PC 1200 executes device control software stored in a ROM 1202 or hard disk (HD) 1211 or supplied via a flexible disk drive (FD) 1212. This PC 1200 totally controls respective devices connected to the system bus 1204.

With the program stored in the CPU 1201, ROM 1202, or hard disk (HD) 1211 of the PC 1200, the procedures of respective steps or the like of the flowcharts of FIG. 2, FIG. 3, FIG. 7, FIG. 9, and FIG. 10 are achieved. Numeral 1203 denotes a RAM, which functions as a main memory, work area, or the like of the CPU 1201. Numeral 1205 denotes a keyboard controller (KBC), which controls an instruction input from a keyboard (KB) 1209, a not illustrated device, or the like.

Numeral 1206 denotes a CRT controller (CRTC), which controls display on the CRT display (CRT) 1210. Numeral 1207 denotes a disk controller (DKC). The DKC 1207 controls access to the hard disk (HD) 1211 and the flexible disk (FD) 1212 which store a boot program, plural applications, edit files, user files, a network management program, and so on. Here, the boot program is a startup program: a program starting execution (operation) of hardware or software of the personal computer.

Numeral 1208 denotes a network interface card (NIC) which exchanges data bi-directionally with a network printer, another network apparatus, or another PC via a LAN 1220.

Next, examples of displaying a fracture risk when a metal sheet is stamped with contour lines will be described with reference to FIG. 12 to FIG. 14.

Figure 12:
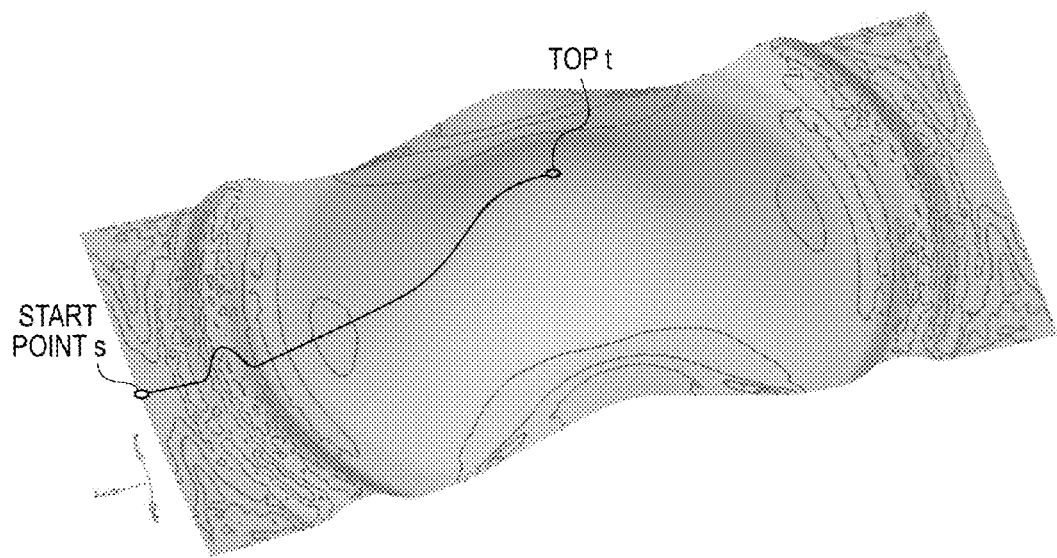
FIG. 12 is a diagram illustrating an example of displaying a fracture risk calculated by a method of comparative example with contour lines.

FIG. 12 is a diagram illustrating a result of displaying the fracture risk calculated using the comparative example $f_1$ with contour lines. As illustrated in FIG. 12, contour lines in the vicinity of the top where the fracture risk is highest are coarse, and the fracture risk portion cannot be identified. On the other hand, in opposite end portions in the longitudinal direction, despite that deformation is quite small, the stress when the portion returned from a plastic state to an elastic state is loaded with a distribution, and thus dense contour lines are formed.

Figure 13:
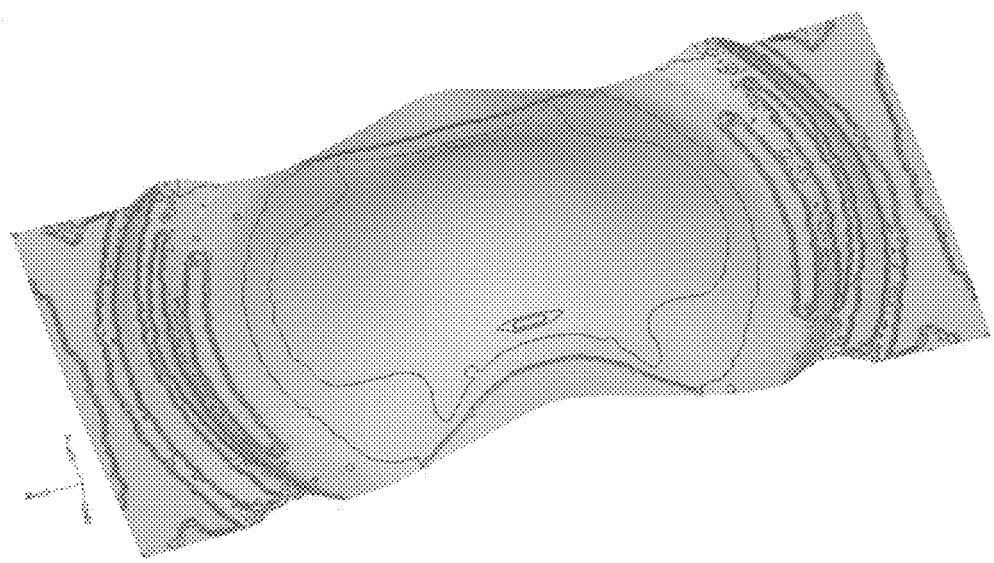
FIG. 13 is a diagram illustrating an example of displaying a fracture risk calculated by a method of first embodiment with contour lines.
Figure 14:
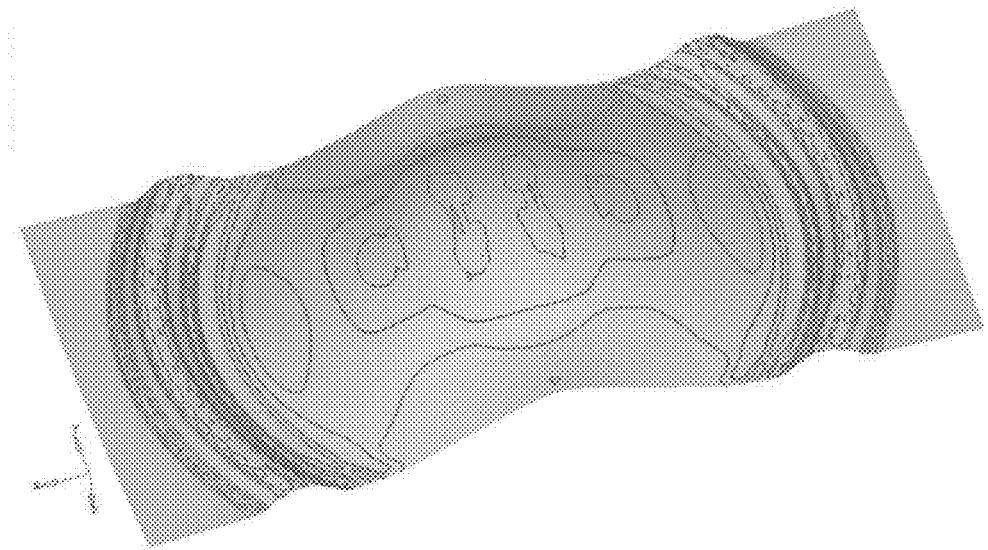
FIG. 14 is a diagram illustrating an example of displaying a fracture risk calculated by a method of second embodiment with contour lines.

FIG. 13 and FIG. 14 are diagrams illustrating results of displaying a fracture risk calculated by the method of the embodiments with contour lines. By displaying the fracture risk calculated by the first embodiment and the second embodiment with contour lines, an accurate fracture risk can be visualized.

FIG. 13 is a diagram illustrating the fracture risk calculated by the method of the first embodiment with contour lines. As illustrated in FIG. 13, the high fracture risk is clearly displayed in the vicinity of the top in the center of the metal sheet. Further, among the contour lines illustrated in FIG. 13, contour lines are coarse in portions where deformation is small in opposite end portions in the longitudinal direction compared to FIG. 12, and it can be seen that the fracture risk is low.

FIG. 14 is a diagram illustrating the fracture risk calculated by the method of the second embodiment with contour lines. Among the contour lines illustrated in FIG. 14, the distribution of the fracture risk in the vicinity of the top in the center of the metal sheet is displayed in further detail, and it can be seen that the fracture risk is high slightly outside the top. Further, among the contour lines illustrated in FIG. 14, it can be seen that the fracture risk is quite small in portions where a deformation is small in opposite end portions in the longitudinal direction. It can be seen that this point sensuously matches conventional experiences.

Figure 15:
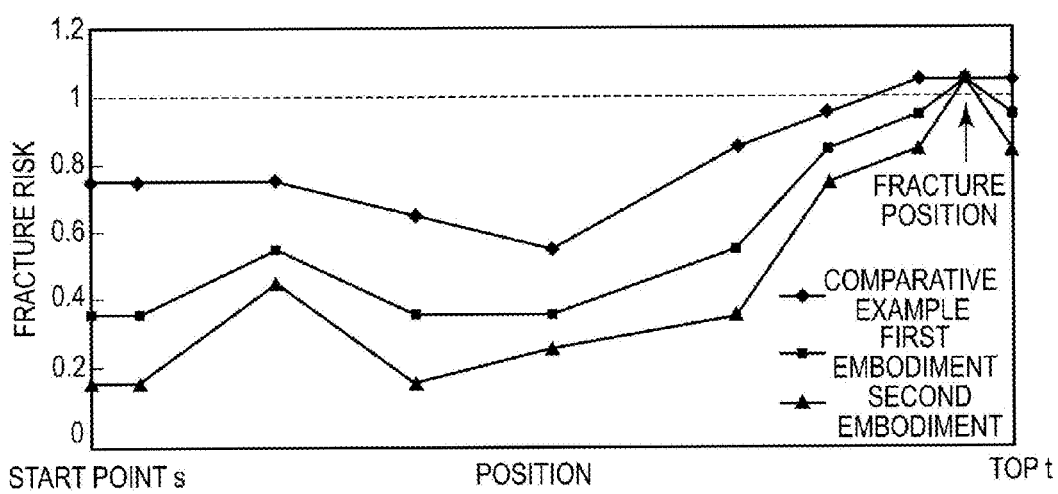
FIG. 15 is a diagram illustrating contour lines of fracture risks from start point s to top t.

FIG. 15 is a diagram illustrating the contour lines illustrated in FIG. 12 to FIG. 14 along a path from start point s to top t as illustrated in FIG. 12. Note that FIG. 15 illustrates contour lines in a state of being further deformed from the deformation states illustrated in FIG. 12 to FIG. 14. The horizontal axis represents the position from the start point s to the top t, and the vertical axis represents the fracture risk. As illustrated in FIG. 15, an actually fractured position is in the vicinity of the top. With contour lines of the fracture risk calculated using the comparative example $f_1$, it is difficult to accurately identify the position to fracture. On the other hand, with contour lines of the fracture risk calculated using the first embodiment, it is possible to identify the position to fracture to a certain degree, and this position substantially matched the position which is actually fractured by experiment. Moreover, with contour lines of the fracture risk calculated using the second embodiment, the difference between the fracture position and the fracture risk of other positions is clear, and it is possible to identify the position to fracture more accurately.

Thus, in the embodiments, the degree of the fracture risk can be evaluated with high accuracy in every fracture determination target portion even when a complicated deformation is involved. Further, visualizing the fracture risk can facilitate intuitive understanding, and thus it is advantageous for considering measures.

Further, even when unloading occurs, the fracture risk will not change, and it is possible to recognize ductility which remains substantially. Further, the fracture risk may be converted into a deformation margin and displayed, which can further facilitate intuitive understanding.

Specific effects of the embodiments are as follows.

1) The fracture risk can be calculated according to damage which a metal structure has received, and thus it does not cause misunderstanding that it is recovered from damage during unloading.

2) By converting into an equivalent plastic strain, a portion where the risk of fracture is high can be evaluated in more detail. Further, contour lines in a portion where the fracture risk is low can be made coarse, and thus deviation regarding the risk of fracture from conventional experiences can be made small.

In the foregoing, the present invention has been described together with various embodiments, but the invention is not limited only to these embodiments, and modifications or the like can be made within the scope of the invention. Note that the fracture determination according to the embodiments may be suitable for ones in which a strain and a stress have occurred along a flat plane having x axis and y axis in a fracture determination target portion of a metal structure, and any strain and stress in z axis direction orthogonal to the x axis and y axis can be ignored.

INDUSTRIAL APPLICABILITY

The present invention can be used for crash simulation of an automobile or stamping simulation of a part.

The invention claimed is:

1. A fracture determination method for determining a fracture of a metal structure, the method comprising:
a deformation analyzing step of performing deformation analysis from start of deformation to end of deformation of the metal structure; and
a fracture determination step of extracting a fracture determination target portion from a deformation state of the metal structure obtained in the deformation analyzing step, and when the extracted fracture determination target portion has returned from a plastic state to an elastic state,
given that a stress when the portion returned to the elastic state is (x, y)=($\sigma 2$, $\sigma 1$) (maximum principal stress: $\sigma 1$, minimum principal stress: $\sigma 2$) on a (x, y) coordinate plane,
performing fracture determination of the fracture determination target portion using a re-yield stress determined by an intersection between a straight line satisfying a relation y=($\sigma 1/\sigma 2$)x and an yield curve obtained from the plastic state of the fracture determination target portion.

2. The fracture determination method according to claim 1, wherein
in the fracture determination step, there are obtained:
a coordinate point of an initial plastic stress determined by an intersection between the straight line satisfying the relation y=($\sigma 1/\sigma 2$)x and an yield curve of an initial state of the fracture determination target portion; and
a coordinate point of a fracture limit stress determined by an intersection between the straight line satisfying the relation y=($\sigma 1/\sigma 2$)x and a fracture limit stress line of the fracture determination target portion, and
wherein a fracture risk of the fracture determination target portion is calculated using a distance from the coordinate point of the initial plastic stress to the coordinate point of the fracture limit stress and a distance from the coordinate point of the initial plastic stress to a coordinate point of the re-yield stress.

3. The fracture determination method according to claim 1, wherein
in the fracture determination step,
a fracture limit stress determined by an intersection between the straight line satisfying the relation y=($\sigma 1/\sigma 2$)x and a fracture limit stress line of the fracture determination target portion is obtained, and
a fracture limit equivalent plastic strain corresponding to the fracture limit stress and an equivalent plastic strain corresponding to the re-yield stress are obtained using an equivalent stress-equivalent plastic strain curve, and
wherein a fracture risk of the fracture determination target portion is calculated using the fracture limit equivalent plastic strain and the equivalent plastic strain.

4. The fracture determination method according to claim 1, wherein
in the fracture determination step,
a coordinate point of a fracture limit stress determined by an intersection between the straight line satisfying the relation y=($\sigma 1/\sigma 2$)x and a fracture limit stress line of the fracture determination target portion is obtained, and
wherein a fracture risk of the fracture determination target portion is calculated using a distance from an origin to the coordinate point of the fracture limit stress and a distance from the origin to a coordinate point of a stress when the portion returned to the elastic state.

5. A fracture determination apparatus determining a fracture of a metal structure, the apparatus comprising:
a deformation analyzing unit performing deformation analysis from start of deformation to end of deformation of the metal structure; and
a fracture determination unit extracting a fracture determination target portion from a deformation state of the metal structure obtained in the deformation analyzing unit, and when the extracted fracture determination target portion has returned from a plastic state to an elastic state,
given that a stress when the portion returned to the elastic state is (x, y)=($\sigma 2$, $\sigma 1$) (maximum principal stress: $\sigma 1$, minimum principal stress: $\sigma 2$) on a (x, y) coordinate plane,
performing fracture determination of the fracture determination target portion using a re-yield stress determined by an intersection between a straight line satisfying a relation y=($\sigma 1/\sigma 2$)x and an yield curve obtained from the plastic state of the fracture determination target portion.

6. A computer implemented program for determining a fracture of a metal structure, the program having instructions when executed by a processor causing a computer to execute:
a deformation analyzing step of performing deformation analysis from start of deformation to end of deformation of the metal structure; and
a fracture determination step of extracting a fracture determination target portion from a deformation state of the metal structure obtained in the deformation analyzing step, and when the extracted fracture determination target portion has returned from a plastic state to an elastic state,
given that a stress when the portion returned to the elastic state is (x, y)=($\sigma 2$, $\sigma 1$) (maximum principal stress: $\sigma 1$, minimum principal stress: $\sigma 2$) on a (x, y) coordinate plane, performing fracture determination of the fracture determination target portion using a re-yield stress determined by an intersection between a straight line satisfying a relation $y=(\sigma1/\sigma2)x$ and an yield curve obtained from the plastic state of the fracture determination target portion.

7. A non-transitory computer readable storage medium recording a program for determining a fracture of a metal structure, the program causing a computer to execute:
- a deformation analyzing step of performing deformation analysis from start of deformation to end of deformation of the metal structure; and
- a fracture determination step of extracting a fracture determination target portion from a deformation state of the metal structure obtained in the deformation analyzing step, and when the extracted fracture determination target portion has returned from a plastic state to an elastic state,
- given that a stress when the portion returned to the elastic state is $(x, y)=(\sigma2, \sigma1)$ (maximum principal stress: $\sigma1$, minimum principal stress: $\sigma2$) on a $(x, y)$ coordinate plane,
- performing fracture determination of the fracture determination target portion using a re-yield stress determined by an intersection between a straight line satisfying a relation $y=(\sigma1/\sigma2)x$ and an yield curve obtained from the plastic state of the fracture determination target portion.

* * * * *

UNITED STATES PATENT AND TRADEMARK OFFICE
CERTIFICATE OF CORRECTION

PATENT NO. : 8,606,532 B2  Page 1 of 2
APPLICATION NO. : 13/634341
DATED : December 10, 2013
INVENTOR(S) : Shunji Hiwatashi et al.

It is certified that error appears in the above-identified patent and that said Letters Patent is hereby corrected as shown below:

On the Title Page
Abstract, line 10, change "and an yield curve" to -- and a yield curve --;

In the Specification
Column 3, line 14, change "and an yield curve" to -- and a yield curve --;
Column 3, line 31, change "and an yield curve" to -- and a yield curve --;
Column 3, line 48, change "and an yield curve" to -- and a yield curve --;
Column 3, line 66, change "and an yield curve" to -- and a yield curve --;
Column 12, line 16, change "$\epsilon_{eq}^{P}$" to -- $\varepsilon_{eq}^{P}$ --;
Column 12, line 17, change "$\epsilon_{eq}^{B}$" to -- $\varepsilon_{eq}^{B}$ --;
Column 12, line 44, change "$\epsilon_{eq}^{P}$" to -- $\varepsilon_{eq}^{P}$ --;
Column 12, line 45, change "$\epsilon_{eq}^{B}$" to -- $\varepsilon_{eq}^{B}$ --;
Column 12, line 49, change "$\epsilon_{eq}^{P}$" to -- $\varepsilon_{eq}^{P}$ --;
Column 12, line 50, change "$\epsilon_{eq}^{B}$" to -- $\varepsilon_{eq}^{B}$ --;
Column 12, line 52, change "$\epsilon_{eq}^{P}$" to -- $\varepsilon_{eq}^{P}$ --;
Column 12, line 53, change "$\epsilon_{eq}^{B}$" to -- $\varepsilon_{eq}^{B}$ --;

Column 14, line 18, change "$\sigma_{eq}=(\epsilon_{eq}+\epsilon_0)^n$ or $\sigma_{eq}=C\epsilon_{eq}^n$," to -- $\sigma_{eq}=(\varepsilon_{eq}+\varepsilon_0)^n$ or $\sigma_{eq}=C\varepsilon_{eq}^n$, --;
Column 14, line 28, change "$\epsilon_1$" to -- $\varepsilon_1$ --;
Column 14, line 29, change "$\epsilon_2$" to -- $\varepsilon_2$ --;
Column 14, line 38, change "$\epsilon_1$" to -- $\varepsilon_1$ --;
Column 14, line 38, change "$\epsilon_2$" to -- $\varepsilon_2$ --;
Column 14, line 45, change "$\epsilon_{eq}$" to -- $\varepsilon_{eq}$ --;
Column 14, line 46, change "$\epsilon_{ij}$" to -- $\varepsilon_{ij}$ --;

In the Claims
Column 19, line 51, change "and an yield curve" to -- and a yield curve --;
Column 19, line 59, change "and an yield curve" to -- and a yield curve --;

Signed and Sealed this
Twelfth Day of August, 2014

Michelle K. Lee
*Deputy Director of the United States Patent and Trademark Office*

CERTIFICATE OF CORRECTION (continued)
U.S. Pat. No. 8,606,532 B2

Column 20, line 49, change "and an yield curve" to -- and a yield curve --;
Column 21, line 4, change "and an yield curve" to -- and a yield curve --;
Column 21, line 26, change "and an yield curve" to -- and a yield curve --.